United States Patent [19]

Clemens et al.

[11] Patent Number: 4,464,170
[45] Date of Patent: Aug. 7, 1984

[54] BLOOD GLUCOSE CONTROL APPARATUS AND METHOD

[75] Inventors: A. H. Clemens, Elkhart, Ind.; David L. Hough, Edwardsburg, Mich.

[73] Assignee: Miles Laboratories, Inc., Elkhart, Ind.

[21] Appl. No.: 428,381

[22] Filed: Sep. 29, 1982

[51] Int. Cl.$^3$ .............................................. A61M 5/00
[52] U.S. Cl. ............................ 604/50; 128/DIG. 13
[58] Field of Search .................... 604/2, 4, 50, 66–67; 128/632–633, DIG. 13

[56] References Cited

U.S. PATENT DOCUMENTS

| | | | |
|---|---|---|---|
| 4,077,405 | 3/1978 | Haerten et al. | 604/66 |
| 4,151,845 | 5/1979 | Clemens | 604/66 |
| 4,245,634 | 1/1981 | Albisser et al. | 604/66 |

OTHER PUBLICATIONS

Fukui, Y. et al., "Digital and Sampled-Data Control of Arterial Blood Pressure During Halothane Anesthesia", Proc. of the San Diego Biomedical Symposium, 1974, pp. 273–278.

Primary Examiner—Kyle L. Howell
Assistant Examiner—Francis J. Jaworski
Attorney, Agent, or Firm—Roger N. Coe

[57] ABSTRACT

In a method and apparatus for controlling the concentration of glucose in the blood stream of a subject at a desired level (BI) including controlling the supply of insulin (IR) by periodically measuring the blood glucose concentration (G) and selecting a predetermined basal infusion rate (RI) for the desired level, the step of selecting a predetermined basal infusion rate comprises periodically searching for the value of the basal infusion rate RI required for BI in accordance with $$RI = RI_{LAST}(GY/BI)$$

where (GY) is the present blood glucose level corrected to fit a least squares regression line, when the slope of the least squares regression line fit for the last five G values is less than 0.5 and GY is within ±50% of the desired BI level, and wherein the period between searches is equal to or greater than the period between glucose measurements.

4 Claims, 1 Drawing Figure

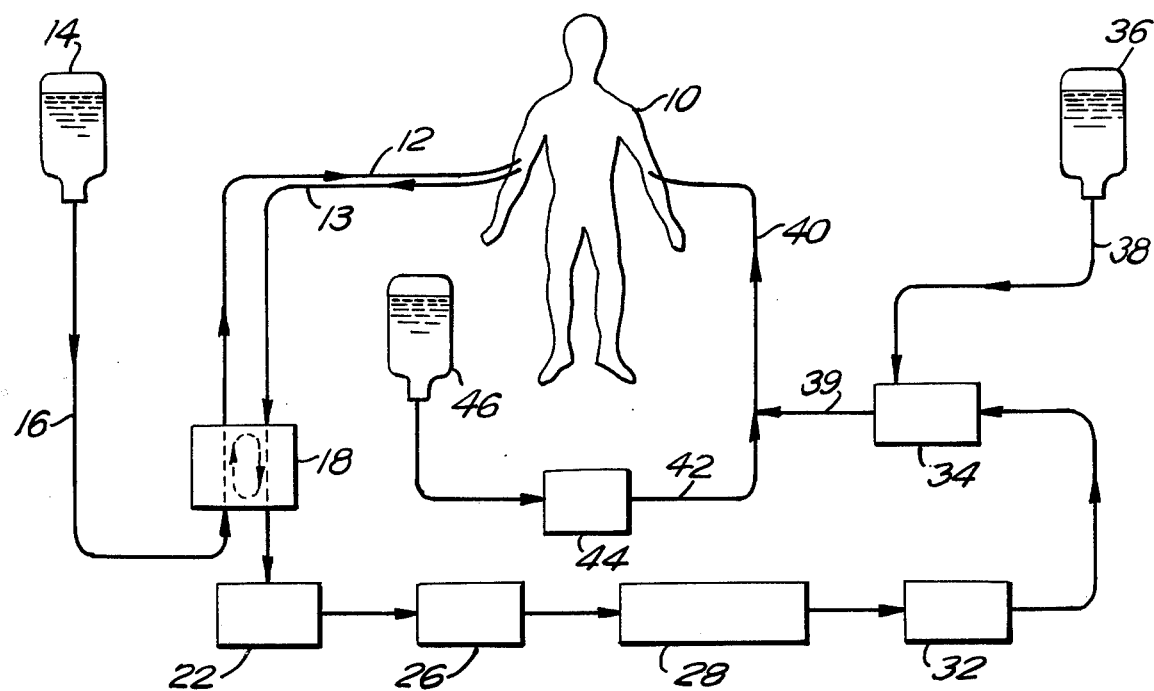

BLOOD GLUCOSE CONTROL APPARATUS AND METHOD

BACKGROUND OF THE INVENTION

The present invention relates to glucose monitoring systems in general and, more particularly, to an improvement in the method and apparatus for controlling blood glucose concentrations in a subject by selected infusion of insulin.

Methods and apparatus for the analysis of blood glucose concentration and the infusion of insulin based upon such analysis are known in the prior art, as can be found in U.S. Pat. No. 4,151,845.

In systems such as the one aforementioned, the concentration of glucose in the bloodstream of a subject is controlled by infusion of insulin to the subject dependent upon the concentration of glucose in the subject's bloodstream. In such an apparatus, means are provided for determining the serial values of blood glucose concentration in the blood from minute-to-minute and for providing computer input signals corresponding to those serial values to an interface which in turn controls infusion means connected thereto and to a source of insulin. The infusion means is responsive to the output of the interface for introducing insulin from the source into the bloodstream at a rate determined thereby. The computer is programmed to provide, in response to its input signals, output signals which cause the infusion of insulin in accordance with an algorithm wherein there is a required basal infusion rate RI for the desired basal or steady state glucose concentration BI for that patient.

In such systems, the required basal infusion rate RI for a desired basal or steady state glucose concentration has been estimated for each subject and thereafter an operator used trial and error to achieve the correct value, however, until the correct value was reached, the apparatus was not able to achieve the desired basal steady state glucose concentration.

SUMMARY OF THE INVENTION

The main object of the present invention is to provide a control algorithm to be used with continuous blood sugar measuring and insulin infusion systems to cause the actual blood sugar level to achieve the same level as that said for the constant steady state glucose concentration BI. This is achieved by slowly changing the heretofore constant RI or required basal infusion rate at BI, when conditions warrant, to search for the insulin infusion levels which will cause the blood sugar to seek the level set as BI. The search algorithm works by slowly changing the constant required basal infusion rate RI at the desired basal or steady state glucose concentration BI which is a multiplier in the insulin determination algorithm.

In accordance with the invention, the changing of the constant RI is done in accordance with the following where GY is the present blood glucose level corrected to fit a least squares regression line:

$$RI = RI_{LAST}(GY/BI)$$

The search or updating of the value for RI is done only if M, the slope of the least squares regression line fit for the last five measured blood glucose level values (G), is less than 0.5 (that is the average blood glucose level is changing less than ½ G/min.) and it is only applied if the present GY value is within ±50% of the desired BI level. Moreover, the period between searches is equal to or greater than the period between glucose measurements. Preferably, the searching is applied once every 10 minutes.

In a preferred embodiment, the glucose level is measured every minute and the searching takes place every 10 minutes.

In a particularly advantageous commercial embodiment, it is intended that the present invention be used with the apparatus disclosed in U.S. Pat. No. 4,151,845 and the disclosure thereof is incorporated herein by reference.

BRIEF DESCRIPTION OF THE DRAWINGS

Other and further objects, advantages and features of the invention will be apparent to those skilled in the are from the following detailed description thereof, taken in conjunction with the accompanying drawing wherein the FIGURE is a schematic view of the apparatus according to the present invention for carrying out the method according to the present invention.

DETAILED DESCRIPTION OF THE INVENTION

As shown schematically in the FIGURE, blood is removed from the blood stream of subject 10 by suitable means, such as through a double lumen catheter (not shown), which also introduces an anticoagulant such as heparin, in line 12, which is mixed with the blood as it leaves the subject, thereby diluting the blood passing through line 13. The anticoagulant is stored in reservoir 14 and is pumped to the catheter through lines 16 and 12 by suitable means, such as peristaltic pump 18, which also pumps diluted blood from the catheter through line 13 in the opposite direction. Pump 18 runs continuously to drive the diluted blood from line 13 into glucose analyzer 22.

Glucose analyzer 22 can take a variety of forms. For example, using a colorimeter approach, diluted blood enters analyzer 22 and is diluted further with a physiological saline solution before being segmented with air into discrete bits to be dialyzed against a glucose oxidase-peroxidase-chromagen reagent. The presence of blood glucose specifically alters the color of the reagent and the optical density of the resulting color is measured by a colorimeter which generates a corresponding output signal. The resulting signal is then fed to analog-to-digital converter 26 which prepares the input signal for digital computer 28.

In a preferred embodiment glucose analyzer 22 is a membrane type polarographic assembly which measures the glucose level of the diluted blood and generates a corresponding signal which is supplied to analog-to-digital converter 26 which prepares the input signal for digital computer 28. Suitable membrane type polarographic apparatus is described, for example, in U.S. Pat. No. 4,092,233. In this U.S. patent a membrane is disclosed containing glucose oxidase which converts glucose to hydrogen peroxide which is detected in the polarographic assembly by a difference in electrical potential.

Analog-to-digital converter 26 feeds the digital input signal corresponding to the blood glucose level to computer 28, which is programmed according to an algorithm such as the one set forth in U.S. Pat. No. 4,151,845. Responsive to the signals from analyzer 22, the computer determines the infusion rate of insulin for the subject by use of the algorithm programmed into the computer. Once the infusion rate required by the subject has been determined, digital signals are fed from computer 28 to pump interface 32 which controls the infusion pumping which will now be described. Pump 34 connected to interface 32 receives insulin from reservoir 36 by way of line 38 and feeds the insulin into lines 39 and 40. Line 42 receives saline solution from pump 44, which draws said solution from reservoir 46. Accordingly, insulin from reservoir 36 is mixed with saline solution as it is fed into line 40, and the resulting solution is introduced into the blood stream of subject 10 through a suitable catheter (not shown). A closed loop is therefore provided which includes subject 10.

It will be understood that while the use of a digital computer is preferred, converter 26 and computer 28 can be replaced by an analog computer, if desired. Pump 34 would then be driven in analog fashion rather than in digital fashion.

As will be apparent, the regulation afforded by the structure described with reference to the FIGURE depends on computer algorithms programmable into computer 28. Ideally, the algorithms should be capable of interpreting requirements for insulin to the point where the blood glucose concentration of a subject is maintained substantially constant at a level which is considered normal for the subject in question. An insulin dependent diabetic requires a static insulin release supplemented by a dynamic control function.

The present invention provides an improvement in algorithms for achieving static and/or dynamic control of the blood glucose level which are dependent upon the minute-by-minute measurements of the present glucose concentration in the blood stream and the predetermined required basal insulin infusion rate RI at BI which is the desired basal or steady state glucose concentration.

In order to achieve the proper constant RI for the particular person being treated so that insulin infusion levels will be applied which will cause the blood sugar to seek the level set at BI, the algorithm according to the present invention enables the system to search for a constant RI by slowing changing same in successive updatings until the proper RI is reached for the patient. The algorithm applied is as follows:

$$RI = RI_{LAST}(GY/BI)$$

where (GY) is the present blood glucose level corrected to fit a least squares regression line, when the slope of the least squares regression line fit for the last five G values is less than 0.5 and GY is within ±50% of the desired BI level, and wherein the period between searches is equal to or greater than the period between glucose measurements.

Thus, in the past while the operator of the system had to approximate an RI for each patient and slowly change the value RI by a trial and error method. The algorithm according to the present invention allows the computer to slowly search and find the proper constant RI automatically without any overshooting and thus no danger to the patient.

It will be appreciated that the instant specification and claims are set forth by way of illustration and not limitation, and that various modifications and changes may be made without departing from the spirit and scope of the present invention.

What is claimed is:

1. In an apparatus for controlling the concentration of glucose in the blood stream of a subject at a desired level (BI) having means for controlling the infusion rate of insulin as a function of the periodically measured blood glucose concentration (G) and a predetermined basal infusion rate (RI) for the desired level, the improvement comprising means for periodically searching for and determining the basal infusion rate RI for the desired level in accordance with:

$$RI = RI_{LAST}(GY/BI)$$

said means for searching and determining including means for determining the present blood glucose concentration value (GY), means for fitting a plurality of blood glucose concentrations (G) to a least squares regression line and for determining if the slope of the least squares regression line fit for the least five G values is less than 0.5 and if GY is within ±50% of the desired BI level, said means for searching and determining conducting searches at periods equal to or greater than the period between glucose measurements.

2. The apparatus according to claim 1, wherein the means for controlling the supply of insulin as a function of the periodically measured blood glucose concentration measures same minute-to-minute and the means for periodically searching for the basal infusion rate examines the basal infusion rate every 10 minutes.

3. In a method for controlling the concentration of glucose in the blood stream of a subject at a desired level (BI) including controlling the supply of insulin by periodically measuring the blood glucose concentration (G) and selecting a predetermined basal infusion rate (RI) for the desired level, the improvement wherein the step of selecting a predetermined basal infusion rate comprises periodically searching for and determining the value of the predetermined basal infusion rate RI required for BI in accordance with $$RI = RI_{LAST}(GY/BI)$$

said steps of searching and determining including determining the present blood glucose concentration (GY), fitting a plurality of blood glucose determinations (G) to a least squares regression line, determining if the slope of the least squares regression line fit for the last five G values is less than 0.5 and if GY is within ±50% of the desired BI level, said steps of searching and determining being conducted at periods equal to or greater than the period between glucose measurements.

4. The method according to claim 3, wherein the glucose concentration is measured minute-to-minute and the periodic measuring is effected every 10 minutes.

* * * * *